United States Patent [19]
Augustine

[11] Patent Number: 5,817,146
[45] Date of Patent: Oct. 6, 1998

[54] PATIENT WARMING SYSTEM WITH IV FLUID WARMER

[75] Inventor: Scott D. Augustine, Bloomington, Minn.

[73] Assignee: Augustine Medical, Inc., Eden Prairie, Minn.

[21] Appl. No.: 552,510

[22] Filed: Nov. 9, 1995

[51] Int. Cl.⁶ .................................................. A61F 7/12
[52] U.S. Cl. ............................... 607/104; 607/107; 5/423
[58] Field of Search .............................. 432/62, 92, 224, 432/225; 34/107, 201, 202, 242; 604/113; 607/96, 108, 114, 107, 104; 5/423

[56] References Cited

U.S. PATENT DOCUMENTS

| | | |
|---|---|---|
| 1,493,450 | 5/1924 | Richardson . |
| 1,995,302 | 3/1935 | Goldstein ................................. 128/254 |
| 2,507,464 | 5/1950 | De Andrade So ........................ 219/39 |
| 3,358,382 | 12/1967 | Glintz ......................................... 34/202 |
| 3,968,346 | 7/1976 | Cooksley ................................. 219/305 |
| 4,047,563 | 9/1977 | Kurata ..................................... 165/158 |
| 4,111,659 | 9/1978 | Bowley ..................................... 422/48 |
| 4,114,620 | 9/1978 | Moore et al. ........................... 128/254 |
| 4,167,663 | 9/1979 | Granzow, Jr. et al. ................ 219/497 |
| 4,177,816 | 12/1979 | Torgeson ................................ 128/400 |
| 4,214,147 | 7/1980 | Kraver ..................................... 219/301 |
| 4,281,238 | 7/1981 | Noma et al. ............................ 219/305 |
| 4,293,762 | 10/1981 | Ogawa ..................................... 219/302 |
| 4,306,018 | 12/1981 | Kirkpatrick ........................... 435/2.261 |
| 4,384,578 | 5/1983 | Winkler ................................... 604/114 |
| 4,532,414 | 7/1985 | Shah et al. ............................. 219/308 |
| 4,572,188 | 2/1986 | Augustine et al. .................... 128/380 |
| 4,653,577 | 3/1987 | Noda ......................................... 165/71 |
| 4,680,445 | 7/1987 | Ogawa ..................................... 219/299 |
| 4,707,587 | 11/1987 | Greenblatt .............................. 219/299 |
| 4,709,135 | 11/1987 | Dietrich et al. ........................ 219/303 |
| 4,734,269 | 3/1988 | Clarke et al. ........................... 422/310 |
| 4,735,609 | 4/1988 | Comeau et al. ........................ 604/114 |
| 4,759,749 | 7/1988 | Verkaart ................................. 604/113 |
| 4,772,778 | 9/1988 | Ogawa ..................................... 219/30 |
| 4,787,883 | 11/1988 | Kroyer .................................... 604/113 |
| 4,833,299 | 5/1989 | Estes ........................................ 219/311 |
| 4,878,537 | 11/1989 | Verkaart ................................. 165/156 |
| 4,900,308 | 2/1990 | Verkaart ................................. 604/126 |
| 4,908,014 | 3/1990 | Kroyer .................................... 604/604 |
| 5,063,994 | 11/1991 | Verkaart ................................. 165/154 |
| 5,074,838 | 12/1991 | Kroyer ................................. 604/4.604 |
| 5,097,898 | 3/1992 | Verkaart ................................. 165/154 |
| 5,106,373 | 4/1992 | Augustine et al. .................... 604/113 |
| 5,125,238 | 6/1992 | Ragan et al. .......................... 62/259.3 |
| 5,179,943 | 1/1993 | Hama et al. ............................ 607/107 |
| 5,214,860 | 6/1993 | Landes ..................................... 34/202 |
| 5,245,693 | 9/1993 | Ford et al. .............................. 392/470 |
| 5,254,094 | 10/1993 | Starkey et al. ......................... 604/113 |
| 5,271,085 | 12/1993 | Carballo ................................. 392/444 |
| 5,300,101 | 4/1994 | Augustine et al. .................... 607/107 |
| 5,405,371 | 4/1995 | Augustine et al. .................... 607/107 |
| 5,443,488 | 8/1995 | Nameneye et al. .................... 607/107 |
| 5,625,960 | 5/1997 | Fujita ....................................... 34/202 |
| 5,651,757 | 7/1997 | Meckstroth ........................... 604/113 |

FOREIGN PATENT DOCUMENTS

WO 807/10946  4/1987  WIPO .................... 604/113

Primary Examiner—Robert L. Nasser
Attorney, Agent, or Firm—Gray Cary Ware Freidenrich

[57] ABSTRACT

A small container such as a syringe or vial of fluid is inserted into a flow of temperature-conditioned gas to warm the fluid. The gas may be used, for example, to inflate a thermal care apparatus that exhausts the gas through a plurality of exhaust ports about a patient to envelop the patient in a warm bath. In one embodiment, the container is inserted into an inflatable chamber of the apparatus, and sealably held in place by a resilient aperture structure. In another embodiment, the container is inserted into through the aperture structure into a fluid supply hose that brings temperature-conditioned gas to the apparatus from a source. The aperture structure may comprise, for example, a selected pattern of perforations defined in the chamber or hose, or a layering of resilient material affixed to the chamber or hose with a suitably shaped aperture for receiving the container.

48 Claims, 10 Drawing Sheets

PATIENT WARMING SYSTEM WITH IV FLUID WARMER

BACKGROUND OF THE INVENTION

1. Field of the Invention

The present invention generally relates to the administration of intravenous ("IV") fluids to a patient. More particularly, the invention concerns a system for the convective warming of a small container of such fluid, such as a syringe or vial, prior to administration.

2. Description of the Related Art

Fluids that are administered intravenously to a patient typically consist of blood-based fluids and non-blood fluids, all referred to as "IV fluids." As is known, blood-based fluids are held in cool storage at approximately 4° C. until they are used. Non-blood fluids are usually stored at room temperature.

Intravenously administered fluids are a major cause of conductive heat loss in patients and can contribute to patient hypothermia. In critical situations, such as during or after surgery, hypothermia poses a significant peril to a patient. When fluid must be intravenously administered to patients in these circumstances, the threat of hypothermia is compounded.

In order to reduce its contribution to hypothermia, an IV fluid may be warmed immediately prior to administration. However, overheating IV fluids may destroy important components of the fluids, such as cells of blood-based compositions.

Presently, it is known to warm IV fluids prior to administering them intravenously. Further, it has been recognized that convection is a safe method for warming IV fluids. Relatedly, there is a reduced risk of overheating the fluid when a gas, such as heated air, is used to transfer thermal energy. U.S. Pat. No. 4,707,587 concerns a blood-warming method using air as a heating medium. The patent discloses a structure that warms blood by flowing it through a blood-warming jacket, which is heated by conductive contact with an airflow apparatus. The jacket includes a serpentine path through which the blood is circulated. Some users may find the jacket to be bulky and cumbersome. The device provides a lengthy single-tube path for blood to flow. This creates a resistance to flow, which may render the device inadequate for handling medium- to high-flow rate applications involving blood at 4° C. in some applications.

U.S. Pat. No. 5,106,373, assigned to the assignee of the present application and incorporated herein by reference, solves many of the problems not resolved by the '587 patent. For example, the IV fluids are placed in the warming location over which heated gas flows, thereby eliminating the need for a potentially cumbersome warming jacket. The '373 patent disclosed that the heated gas may also be conveniently used to operate a patient-warming blanket, such as the airflow cover disclosed in U.S. Pat. No. 4,572,188, also assigned to the assignee of this application and incorporated herein by reference.

A somewhat different tack is taken by U.S. patent application Ser. No. 08/216,139, filed on Mar. 22, 1994, and entitled "Intravenous Fluid-Warming Method and Apparatus", assigned to the assignee of this application and incorporated herein by referenced. The '139 application provides a system to firmly hold the IV fluid in a fixed warming location. Advantageously, the '139 application retains the ability to operate a patient-warming blanket in parallel, thus further decreasing the risk of patient hypothermia.

More particularly, the '139 device delivers fluid from a source, such as an IV bottle, through an inlet tube to a plurality of warming tubes contained within a central bore of a warming conduit heated by a source of warming medium. The plurality of warming tubes effectively increases the cross-sectional area and surface area of the fluid, reducing flow resistance to the system. This also has the effect of increasing the dwell time of the fluid in the stream of heated medium, and hence the amount of heat transferred to the fluid.

In many applications, the above-described fluid-warming techniques have proven to be entirely satisfactory to their users. Some applications, however, present new challenges, especially relating to pediatric patients.

Pediatric patients present special considerations for the clinician. For instance, infants and pediatric patients have large heads and body surface areas relative to their body mass. Consequently, they lose heat rapidly when exposed to the environment. If a pediatric patient loses fluids rapidly, the expeditious infusion of cold fluids in response could have serious hypothermic implications. Additionally, with neonatal patients, doctors must be able to precisely control the total volume of fluids administered. Over-hydration of neonatal patients can inhibit the healthy exchange of gases in the lungs, causing pulmonary edema.

In addition to pediatric patients, other medical applications would benefit from a system for warming small volumes of fluids. For instance, small volumes of fluid are sometimes used to irrigate during surgical procedures. Warmed fluids are also used during skin preparation or debridement to keep the patient normothermic. Also, surgeons occasionally use small volumes of warmed fluids to flush areas of surgery to prevent the conduction of cold temperatures into the wound.

Presently, when a doctor requires a small amount of a warmed fluid, the doctor places a fluid-filled syringe under a warm water mattress or in a warm water bath. These approaches, although possibly adequate for some applications, have a number of drawbacks. First, such a mattress does not provide a uniform heating medium, and the periodic rotation of the syringe occupies an excessive amount of the nursing staffs time and attention. In addition, the syringe may be damaged under the weight of the overlying patient.

With warm water baths, the temperature of the bath must be accurately maintained at the desired temperature to ensure heating of the fluid-filled syringe to that temperature. If not, then the bath temperature must be measured, the appropriate exposure time must be calculated for the syringe, and the presence of the syringe in the bath must be limited to the calculated exposure time. Alternatively, the temperature of the warmed fluid may be periodically measured in anticipation of reaching the ultimate desired temperature. Another problem of warm water baths is that they occupy the nursing staffs valuable time in maintaining and cleansing the bath to prevent microbial contamination of the water.

Therefore, doctors would enjoy a significant benefit by having ability to quickly, efficiently, and conveniently heat relatively small amounts of fluid for rapid infusion into a patient. Doctors and patients alike would benefit if such a system retained the ability to operate a patient-warming system in parallel, thus further decreasing the risk of patient hypothermia.

SUMMARY OF THE INVENTION

Broadly, this invention concerns a method and apparatus to convectively warm a small container of fluid prior to intravenous administration of the fluid. Specifically, a small container such as a syringe or vial of fluid is inserted into a flow of thermally-conditioned gas such as a warmed airstream to gently heat the fluid. The warmed airstream may be used, for example, to inflate a thermal blanket that exhausts warmed air through a plurality of exhaust ports about a patient to bathe the patient in the warmed airstream.

In one embodiment, the container is inserted into an inflatable chamber of the blanket, and sealably held in place by a resilient temperature-treatment aperture structure. When used herein, the term "aperture structure" denotes a structure, or structural feature, that is operated to open an aperture into an enclosure within which a flow of thermally conditioned gas moves. In another embodiment, the container is inserted via the aperture structure into a supply hose that brings a warmed airstream to the blanket from a source. The aperture structure may comprise, for example, a selected pattern of perforations defined in the chamber or hose, or a layering of resilient material affixed to the chamber or hose with a suitably shaped aperture for receiving the container.

The invention affords a number of distinct advantages. Like prior convective heating devices, this invention provides a gentle but effective means for warming IV fluids such as blood. Unlike prior devices, however, the present invention provides heightened speed and convenience in the convective warming of small amounts of fluids.

Namely, the invention provides speed by permitting doctors to directly insert a small syringe or vial of fluid into a warmed airstream, and then easily remove the container when desired. As a result, the invention is especially useful for use with children or other patients with smaller dosage requirements. The invention is convenient to use because there is no need to re-configure an existing IV tube, prepare a heating jacket, or conduct any protracted assembly of hardware components. Unlike prior arrangements, the set-up, maintenance, and operation of this fluid warming apparatus require only small amounts of time and effort by the nursing staff. The invention may advantageously use the heating source of an existing convective warming apparatus, for example. The invention is efficient because the fluid container is evenly heated by bathing the container in a warmed airstream, without requiring nursing staff to undertake fluid temperature measurement, immersion timing, or rotation of the container.

BRIEF DESCRIPTION OF THE DRAWINGS

The nature, objects, and advantages of the invention will become more apparent to those skilled in the art after considering the following detailed description in connection with the accompanying drawings, in which like reference numerals designate like parts throughout, wherein.

DETAILED DESCRIPTION OF THE PREFERRED EMBODIMENTS

The present invention generally concerns a method and apparatus to convectively warm a small container of fluid prior to intravenous administration of the fluid. The container, such as a syringe or vial of fluid, is inserted into a warm airstream to gently heat the fluid.

STRUCTURE

Fundamental Components

Figure 1:
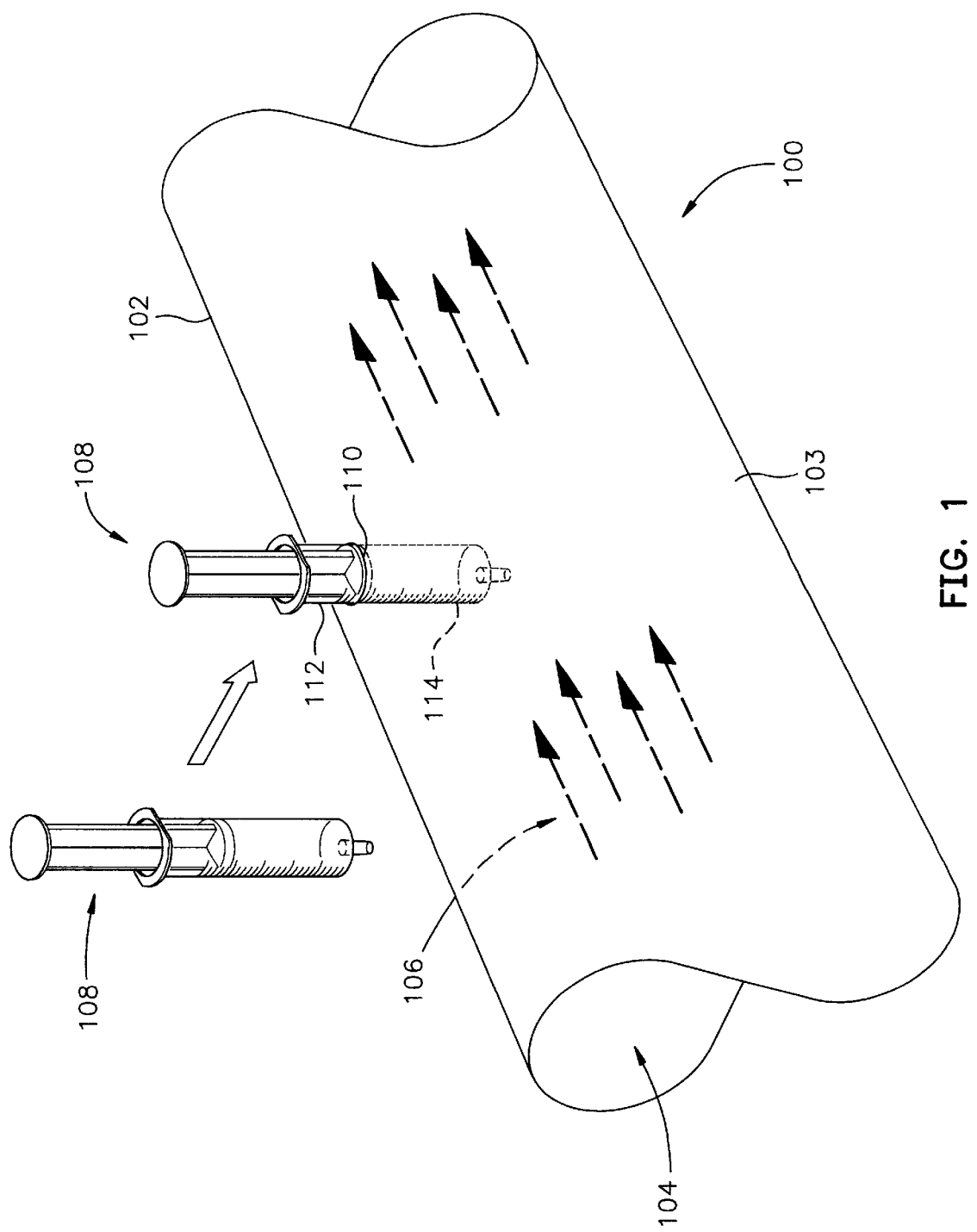
FIG. 1 is a perspective view of the fundamental components of the present invention showing an IV fluid warmer using a flow of thermally-treated gas.

This invention may be implemented using a number of different hardware configurations, as discussed below. Nonetheless, the apparatus aspect of the invention includes an essential complement of components 100 as shown in FIG. 1. The components include a chamber 102 having an outside surface 103 and an internal passage 104 through which a flow 106 of thermally-conditioned gas (such as a warmed airstream) passes. As shown in greater detail below, the chamber 102 may comprise an inflatable structure that constitutes one component of a thermal care apparatus. Alternatively, the chamber 102 may comprise a supply hose that carries a warmed airstream from an airstream source to a thermal care apparatus.

A fluid container 108 is inserted through a resilient temperature-treatment aperture structure 110 provided on the outside surface 103 of the chamber 102. This creates (1) an exposed portion 112 of the container 108, extending outward from the chamber 102, and (2) a concealed portion 114 portion of the container 108, protruding into the internal passage 104 and the warmed airstream 106. While the aperture structure 110 resiliently hugs the container 108, it supports it in place, permitting the warmed airstream to convectively heat the concealed portion 114. When desired, the container 108 can be rapidly and easily removed from the aperture structure 110.

Aperture Structure Construction

Figure 3:
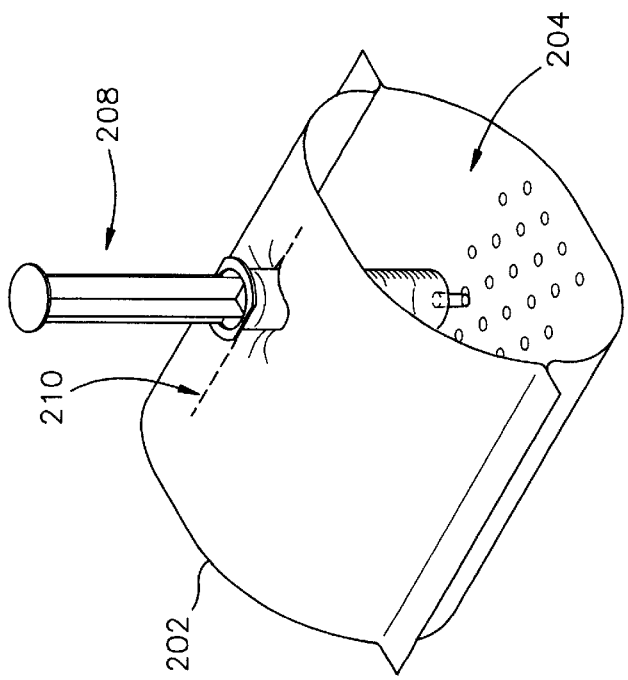
FIG. 3 is a perspective view illustrating the first embodiment of an aperture structure pursuant to the invention, after insertion of the fluid container into the aperture structure.
Figure 2:
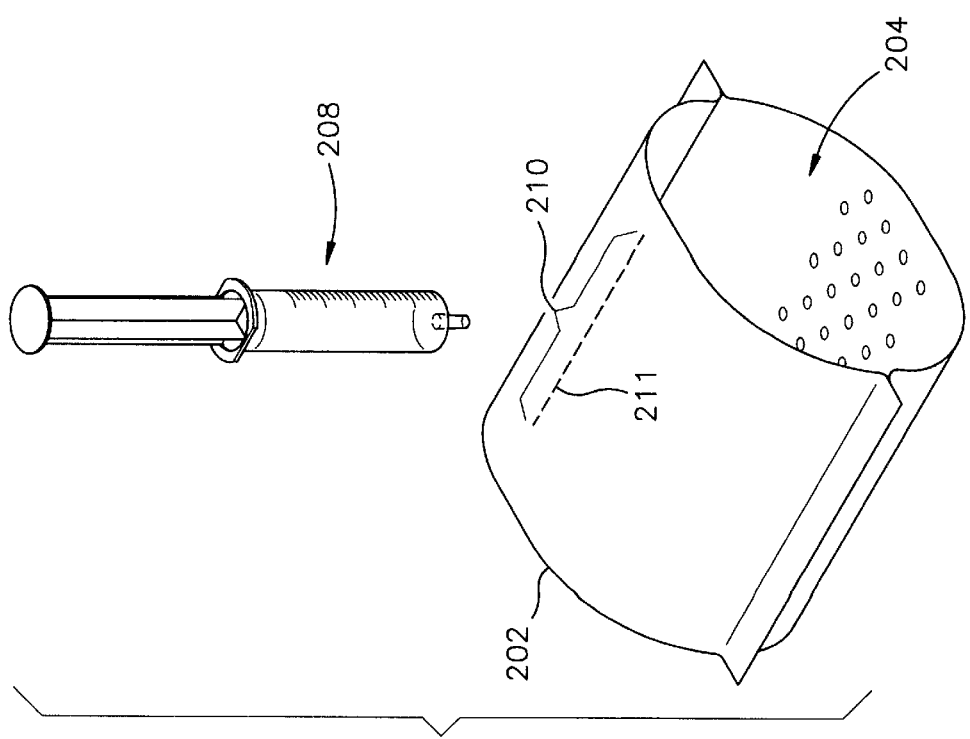
FIG. 2 is a perspective view illustrating a first embodiment of a temperature-treatment aperture structure pursuant to the invention, prior to insertion of a fluid container into the aperture structure.

The temperature-treatment aperture structure 110 may be constructed in various ways from different components. FIGS. 2–3 illustrate a first embodiment, with a chamber 202, internal passage 204, container 208, and aperture structure 210. In this embodiment, the aperture structure 210 comprises an elongated pattern of unopened perforations 211 provided in the chamber 202. The total length of the pattern, as well as each perforation's individual length and separation from adjacent perforations, may be chosen by an ordinarily skilled artisan having the benefit of this disclosure, in view of the size and shape of container. The perforations are preferably defined so that a selected number of perforations may be severed to provide an aperture (or "opening") that snugly receives the container 208 as shown in FIG. 3. In this respect, the individual perforations must not be too large.

To operate the first embodiment aperture structure, the container 208 is inserted through the perforations so that it is supported in a warmed airstream flowing through the internal passage 204. The container and its contents are warmed in the airstream.

Figure 4:
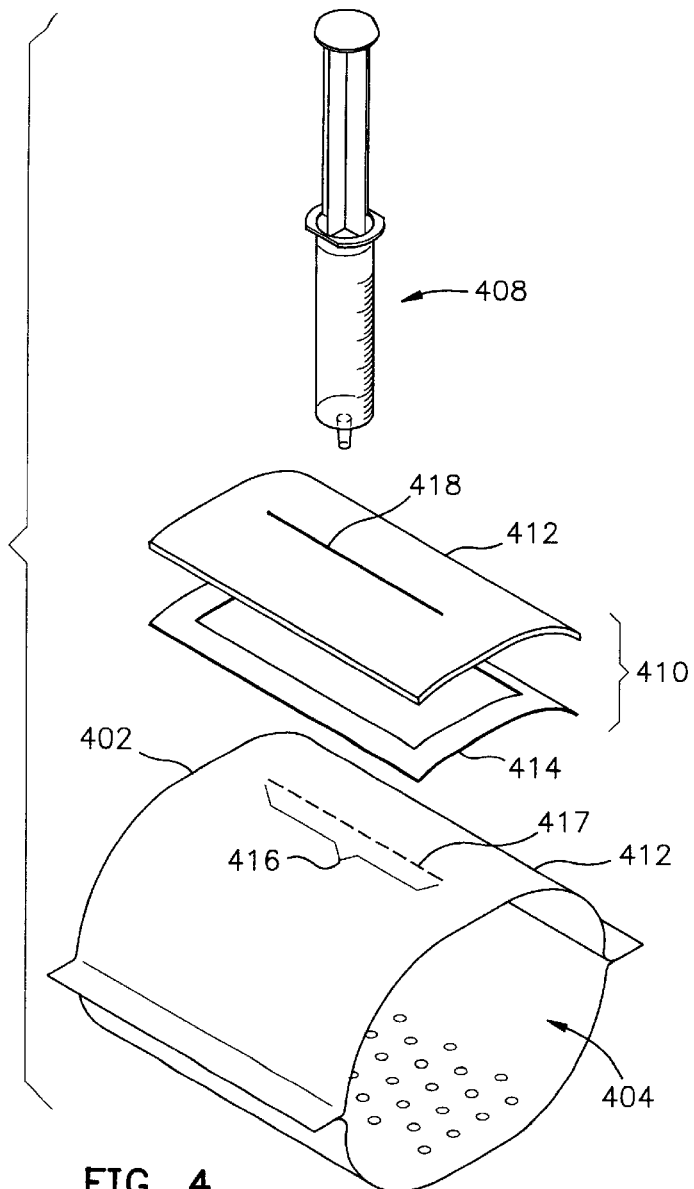
FIG. 4 is an exploded perspective view illustrating a second embodiment of an aperture structure pursuant to the invention, prior to insertion of a fluid container into the aperture structure.
Figure 5:
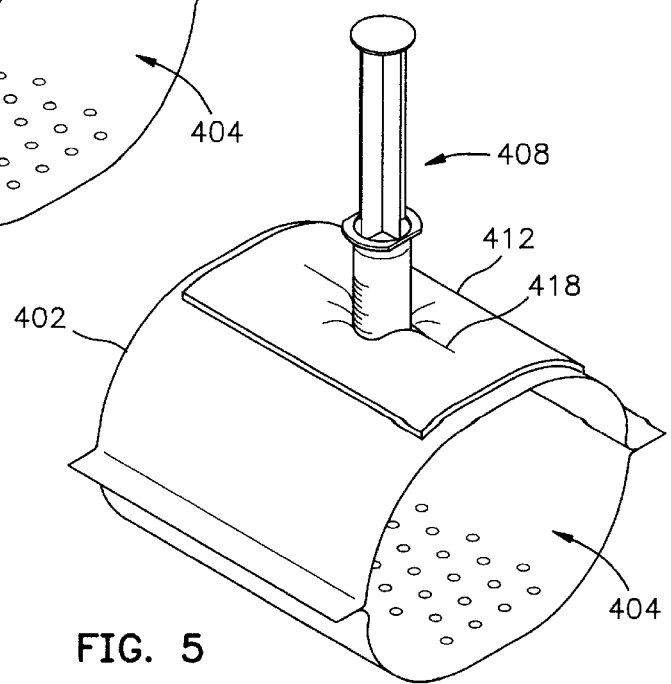
FIG. 5 is a perspective view (assembled) illustrating the second embodiment of an aperture structure pursuant to the invention, after insertion of the fluid container into the aperture structure.

FIGS. 4–5 illustrate an example embodying a second embodiment of an aperture structure. Like the first embodiment, this example includes a chamber 402, an internal passage 404, a container 408, and an aperture structure 410. Here, the aperture structure 410 comprises a cover 412, an adhesive frame 414, and an unopened perforated aperture 416 comprising an elongated pattern of unopened perforations 417. The cover 412 comprises an especially resilient material, such as rubber or open celled polyurethane foam, having a predefined slit 418 predefined in the cover 412. The adhesive layer 414 comprises a peripheral strip of double-sided pressure sensitive adhesive. The unopened, perforated aperture 416 is sized to accept the largest expected size of container 408.

To assemble the aperture structure 410, the adhesive layer 414 is adhered to the chamber 402 about the unopened, perforated aperture 416. Then, the edges of the cover 412 are adhered to the adhesive layer 414, aligning the slit 418 with the unopened, perforated aperture 416.

To operate the aperture structure 410 (FIG. 5), the container 408 is inserted into the slit 418 and pushed through the unopened, perforated aperture 416. The added resiliency of the cover 412 helps to firmly hold the container 408 in place.

After a container of IV fluid is warmed using either of the aperture structures illustrated in FIGS. 2–5, the container is withdrawn in order to administer the fluid. When the container is withdrawn, the airflow integrity of a chamber through which the container is inserted may be restored by, for example, taping over the now-opened perforations.

Figure 6:
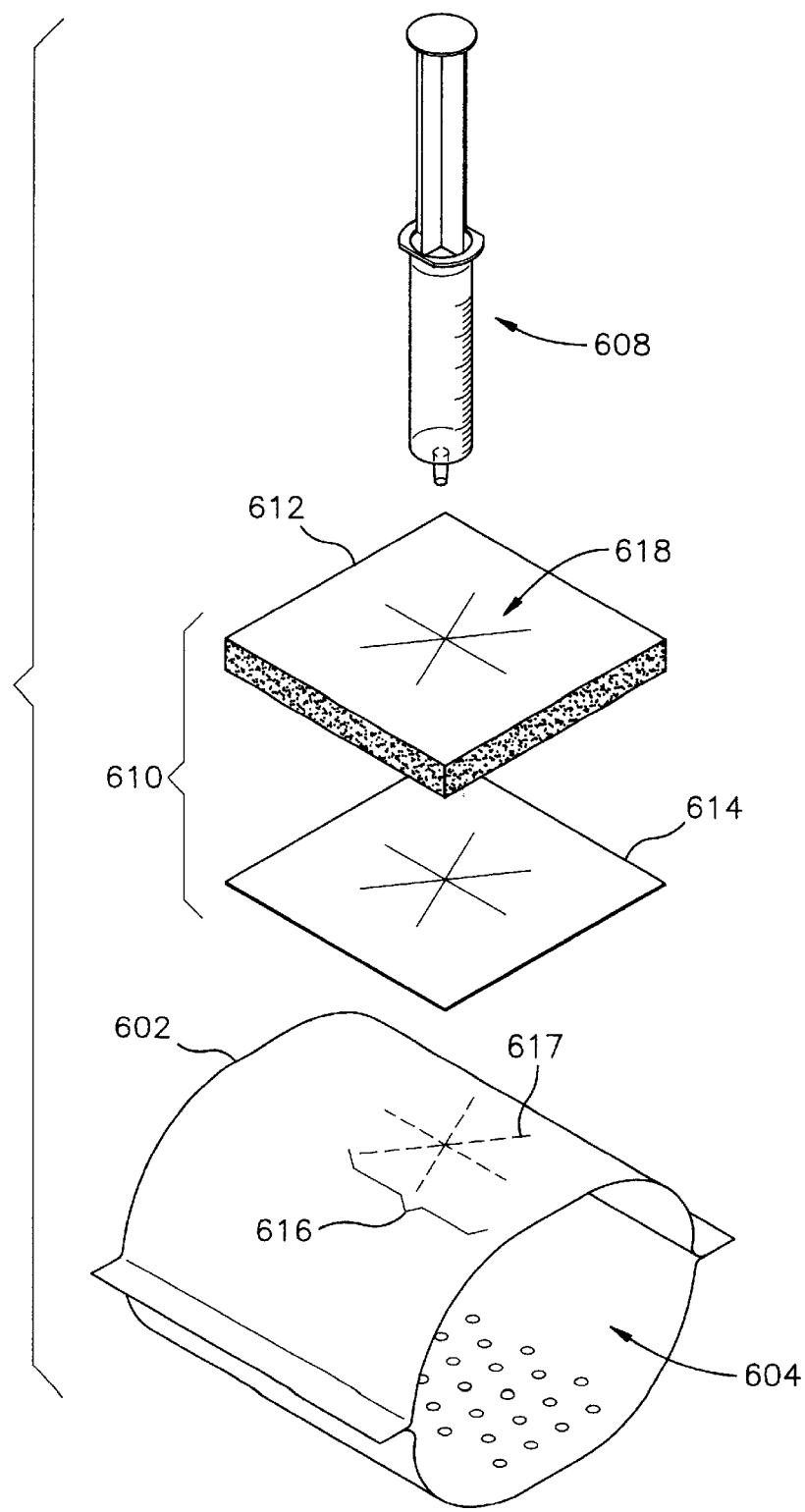
FIG. 6 is an exploded perspective view illustrating a third embodiment of an aperture structure pursuant to the invention, prior to insertion of a fluid container into the aperture structure.
Figure 8:
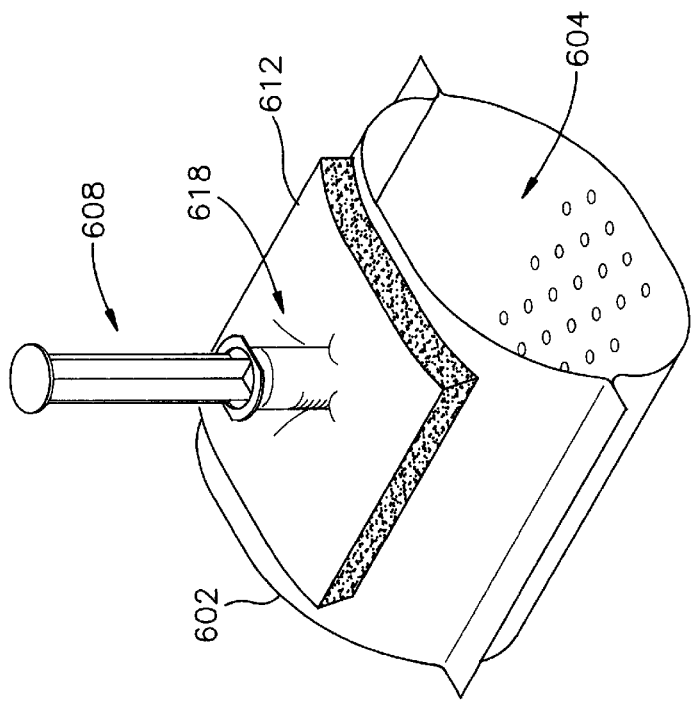
FIG. 8 is a perspective view (assembled) illustrating the third embodiment of an aperture structure pursuant to the invention, after insertion of the fluid container into the aperture structure.
Figure 7:
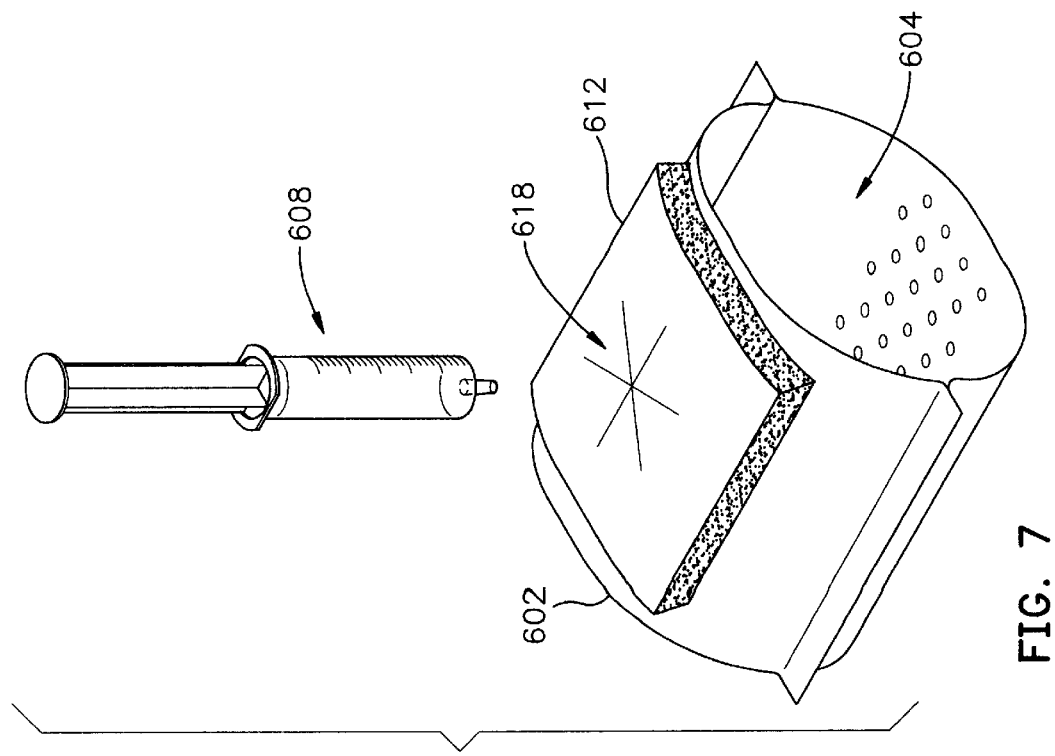
FIG. 7 is a perspective view (assembled) illustrating the third embodiment of an aperture structure pursuant to the invention, prior to insertion of the fluid container into the aperture structure.

FIGS. 6–8 illustrate still another embodiment of the aperture structure 110. Like the first and second embodiments, this embodiment includes a chamber 602, internal passage 604, container 608, and aperture structure 610. Here, the aperture structure 610 comprises a cover 612, an adhesive layer 614, and an unopened, perforated aperture 616 defined in the chamber 602. The cover 612 preferably comprises an especially resilient material, such as open-celled polyurethane foam, having a star-shaped slit 618 predefined therein. The cover 612 may comprise other resilient materials, however, such as rubber, plastic, woven materials, nonwoven materials, etc. The adhesive layer 614 comprises a layer of double-sided pressure sensitive adhesive. The perforated aperture 616 comprises a pre-scored star-shaped set of unopened slits 617, sized to accept the largest expected size of container 608.

To assemble the aperture structure 610, the adhesive layer 614 is adhered to the chamber 602 about the perforated aperture 616. Then, the cover 612 is adhered to the adhesive layer 614, aligning the slit 618 with the perforated aperture 616. The assembled product appears in FIG. 7.

To operate the aperture structure 610 (FIG. 8), the container 708 is inserted through the slit 618 and aperture 616. The added resiliency of the cover 612 helps to firmly hold the container 608 in place. Moreover, after the container 608 is removed, resilient material of the cover 612 "remembers" its unopened state and the star-shaped slit 618 automatically closes itself to self-seal the aperture structure 610.

Implementation

As mentioned above, the present invention may be implemented in a number of different structures. Preferably, the invention is implemented in conjunction with a thermal care unit such as an inflatable thermal blanket used for bathing a patient in a thermally-controlled medium. Such an enclosure may include an inflatable chamber of an inflatable thermal blanket. Such a chamber may include a plurality of exhaust ports to exhaust a thermally-controlled warming medium into a thermal care zone. Typically, an inflatable thermal blanket includes an inlet to receive the thermally-controlled warming medium into the chamber, and forms an enclosure to retain thermally-controlled warming medium within the thermal care zone. The aperture structure is installed so as to sealably receive and support an elongated fluid container of predetermined girth while at least a portion of the container extends into the chamber.

As a more particular example (FIG. 9), the aperture structure of the invention may be implemented in a thermal care apparatus, such as the apparatus 900, for bathing a patient in a warmed inflating medium such as air. The apparatus 900 includes a pair of elongated inflatable members 902–903 interconnected by an access panel 906. The elongated members 902–903 are inflated by a warmed airstream, which is generated by a source such as a heater/blower assembly 914 and delivered through a supply hose 916. The members 902–903 exhaust the warmed air through ports (e.g. 908) to bathe the patient in the warm air. The apparatus 900 may be further understood with reference to U.S. patent application Ser. No. 08/386,989, entitled "Patient Warming System with User- Configurable Access Panel," which was filed on Feb. 6, 1995. The '989 application is hereby incorporated by reference in its entirety.

The heater/blower assembly 914 may comprise a number of different machines. The following references, which are hereby incorporated by reference in their entirety, describe examples of suitable machines. U.S. patent application Ser. No. 08/383,880, entitled "A Source of Inflating Medium with Active Noise Cancellation for an Inflatable Thermal Care Apparatus," filed on Feb. 6, 1995. Another example of a heater/blower assembly is taught by U.S. patent application Ser. No. 08/525,407, entitled "Low Noise Air Blower Unit," filed on Sep. 8, 1995.

Figure 9:
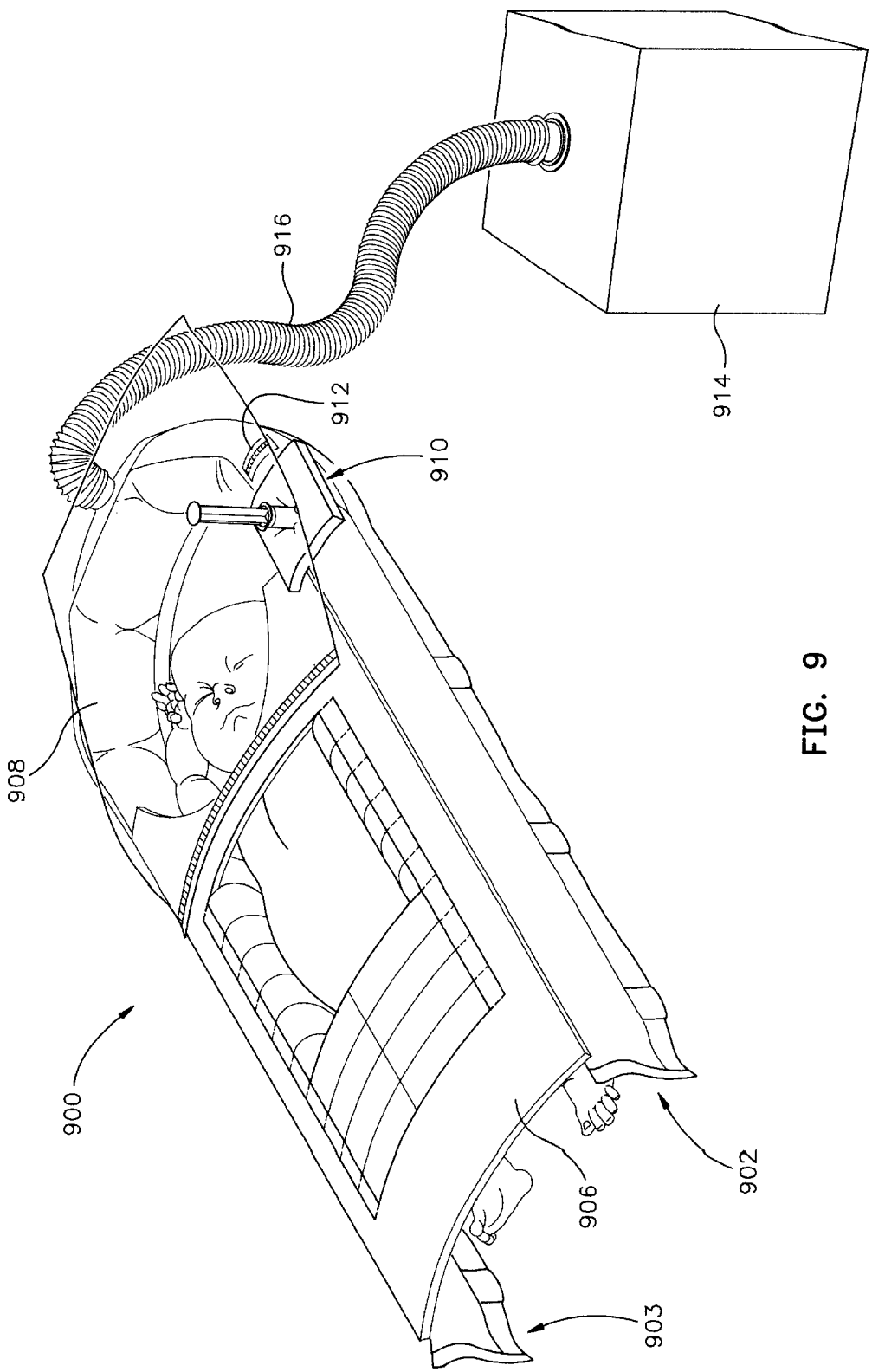
FIG. 9 is a perspective view illustrating a first exemplary implementation of the thermal-treatment aperture structure of the invention with provision for indicating temperature of the flow of thermally-treated gas that warms IV fluid according to the invention.

In the environment of FIG. 9, the aperture structure 910 may be installed in one of the elongated members 902–903, for example, through which a warmed air stream (not shown) passes. Advantageously, the aperture structure 910 may be installed along with a thermometer 912 to measure the temperature of the airstream. As an example, the thermometer 912 may comprise an adhesive strip of thermochromic liquid crystals 912 affixed to the apparatus 900.

As another example (FIG. 10), the aperture structure of the invention may be implemented in a different type of thermal care apparatus for bathing a patient in a thermally-controlled medium. Preferably, the apparatus comprises an inflatable thermal blanket 1000 that includes multiple inflatable, chambers 1002 that expel warmed air through exhaust ports (not shown) to bathe a patient in the warmed air. The inflatable thermal blanket 1000 may be placed, for example, upon a hospital bed 1004.

The chambers 1002 are inflated by a warmed airstream, which is generated by a source 1006 (such as a heater/blower assembly) and delivered through a supply hose 1008. In this environment, the aperture structure 1010 may be installed on an outside surface 1009 of one of the inflatable chambers 1002, through which an airstream passes. The inflatable thermal blanket 1000 may be further understood with reference to U.S. Pat. No. 4,572,188, which has been incorporated by reference in its entirety.

Advantageously, the aperture structure 1010 which facilitates partial insertion of the fluid container 1011 into the air stream (not shown) of a chamber 1002 may be installed along with a thermometer 1012 to measure the temperature of the warmed airstream. As an example, the thermometer 1012 may comprise an adhesive strip of thermochronic liquid crystals 1012 affixed to the blanket 1000.

Figure 11:
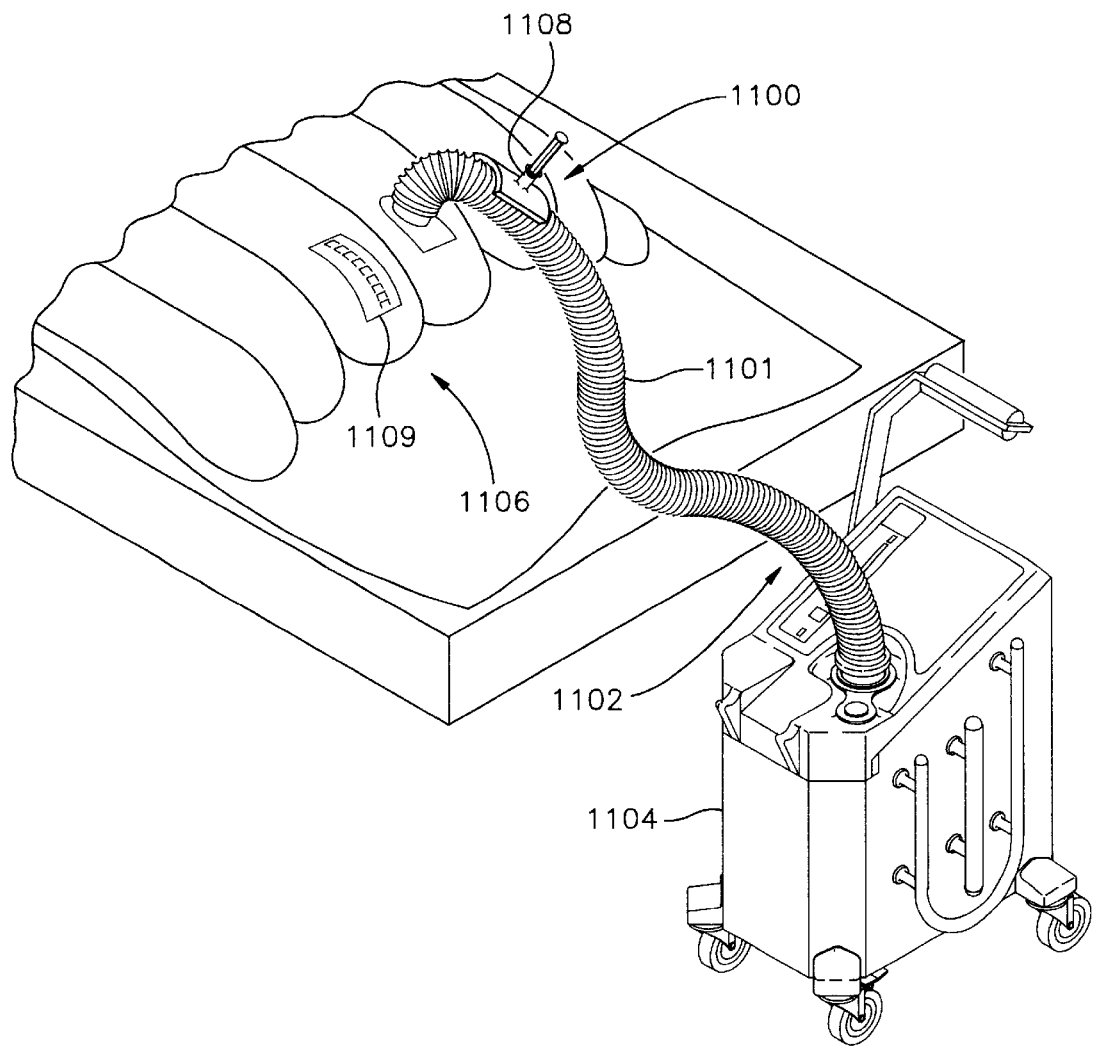
FIG. 11 is a perspective view illustrating a third exemplary implementation of the thermal-treatment aperture structure of the invention with provision for indicating temperature of the flow of thermally-treated gas that warms IV fluid according to the invention.

As shown in FIG. 11, the aperture structure of the invention may be implemented in still another different way. Specifically, an aperture structure 1100 may be installed upon the outside surface 1101 of a supply hose 1102 that delivers a warmed airstream from a source 1104 to a thermal care enclosure 1106. In this embodiment, the aperture structure 1100 is installed by applying techniques, such as those of FIGS. 4–8, to facilitate partial insertion of the fluid container 1108 into the airstream (not shown) of the supply hose 1102.

A thermometer 1109 may be installed at an appropriate location to measure the temperature of the thermally-controlled warming medium. The thermometer 1109 may comprise an adhesive strip of thermochronic liquid crystals affixed to a suitably temperature-responsive area.

OPERATION

Figure 12:
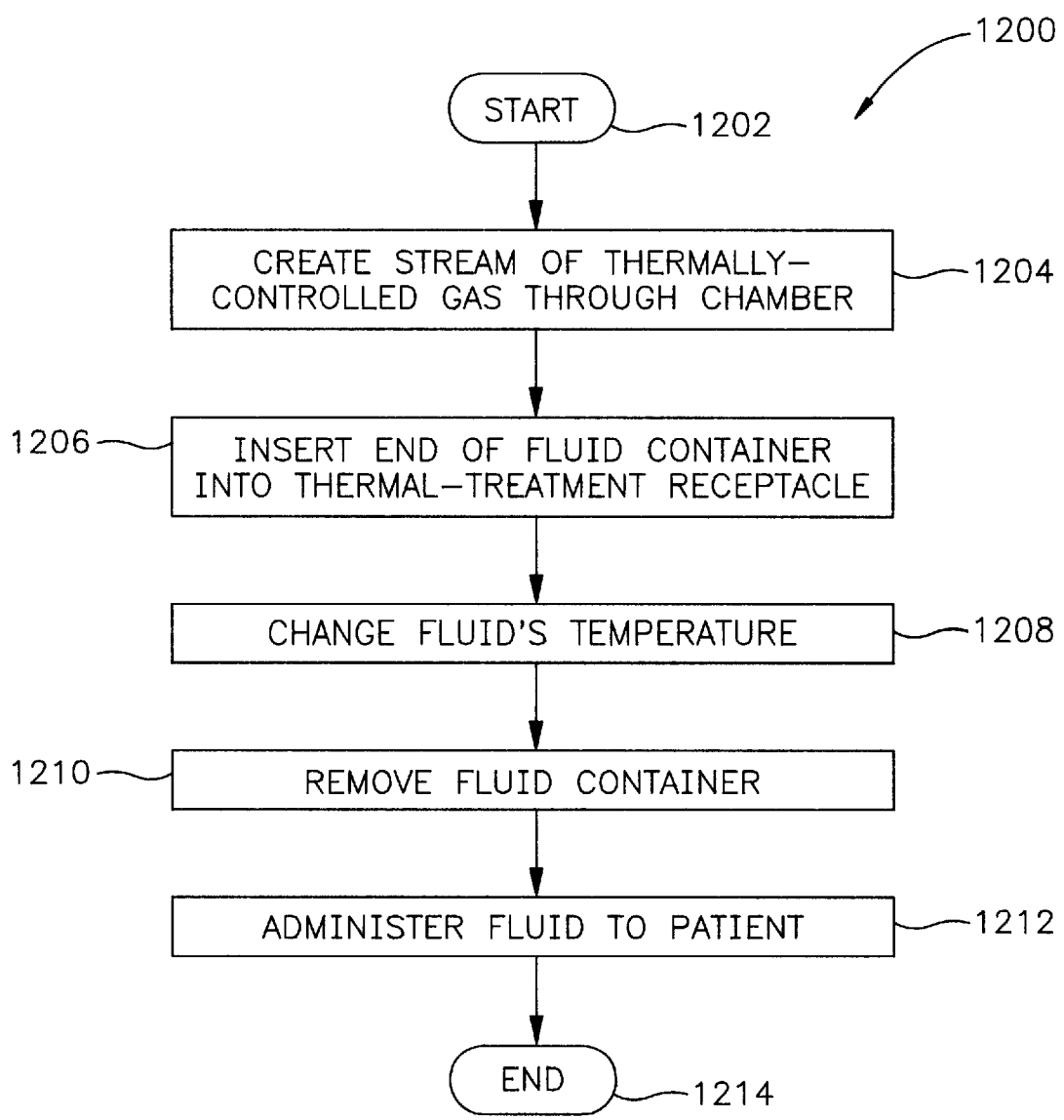
FIG. 12 is a flowchart depicting an illustrative sequence of steps to implement the process of the invention.

In addition to the hardware components described above, the present invention includes a process for the convective temperature treatment a container of fluid. FIG. 12 illustrates a sequence 1200 exemplifying this process. The sequence 1200, which beings in task 1202, is described with reference to hardware components of FIG. 1. In task 1204, a flow of thermally-conditioned gas is passed through a chamber 102 (FIG. 1). As discussed above, the chamber 102 may comprise a portion of an inflatable thermal care enclosure, a supply hose, or another suitable housing for the flow.

Next, an attendant (such as a nurse) inserts the end of a fluid container 108 into the thermal-treatment aperture structure 110. The attendant inserts the container 108 sufficiently into the aperture 104 so that the end 114 is of sufficient size to expose most or all of the fluid to the flow 106. In this position, the aperture structure 110 resiliently supports the container 108. While in this position, the flow 106 warms the fluid in task 1308. In the case of a warmed airstream, for example, the airstream convectively warms the fluid and its container.

When desired, the attendant completely removes the fluid container 108 from the aperture structure 110 in task 1210. This step may be performed, for example, a predetermined time after initially inserting the container 108, where such predetermined time is calculated to fully realize the desired temperature change. Or, the container 108 may be inserted indefinitely, for the attendant's convenient removal when it is needed.

In task 1212, the attendant administers the fluid of the container 108 to the patient. This step may involve injecting the fluid intravenously, providing the fluid to the patient orally, using the fluid to wash or cleanse a wound, or another action. After task 1212, the sequence 1200 ends in task 1214.

Figure 10:
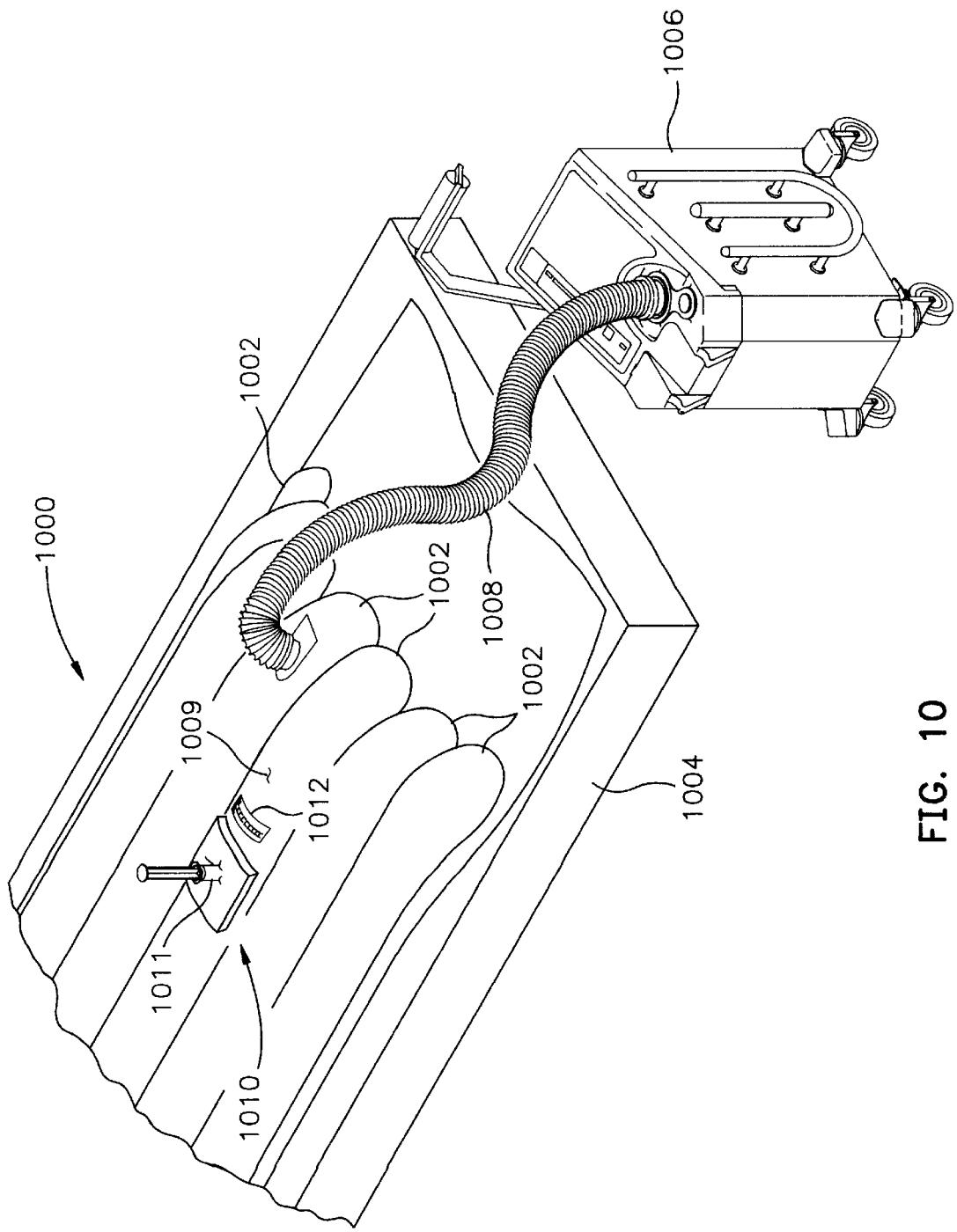
FIG. 10 is a perspective view illustrating a second exemplary implementation of the thermal-treatment aperture structure of the invention with provision for indicating temperature of the flow of thermally-treated gas that warms IV fluid according to the invention.
Figure 13:
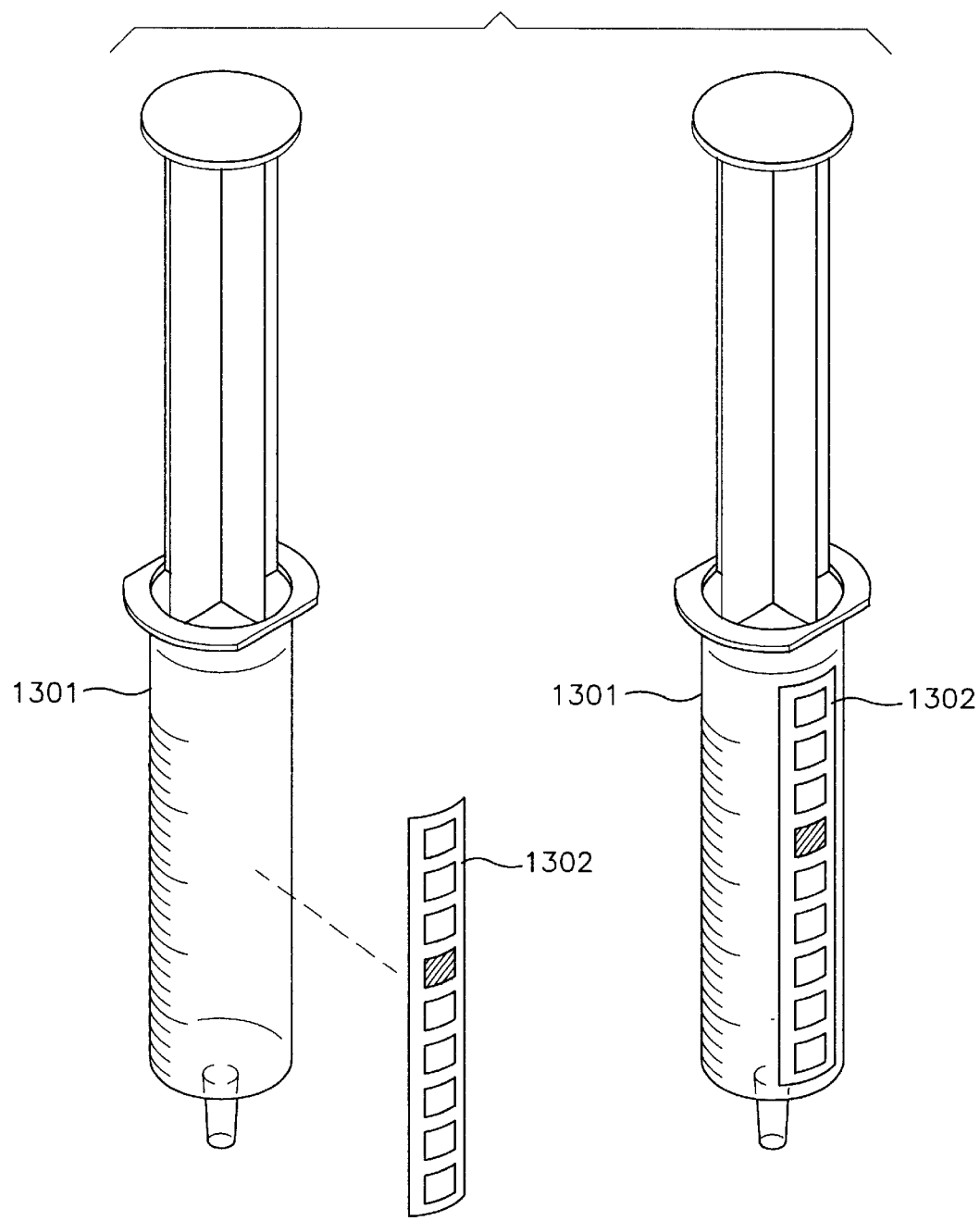
FIG. 13 illustrates an arrangement for measuring temperature of an IV fluid container warmed according to the invention.

FIG. 13 shows an arrangement to more accurately indicate the temperature to which IV fluid in a container has been heated according to the invention. Some estimate of the IV fluid temperature may be gleamed using a thermometer (or other temperature indicator) positioned near the IV fluid container as illustrated in FIGS. 9–11. Such an estimate will be more or less accurate according to many factors. Another, potentially more accurate indication of IV fluid temperature can be obtained using the arrangement of FIG. 13. In FIG. 13, an IV fluid container such as a syringe 1301 has attached to it a thermometer in the form of a strip of thermochronic liquid crystals 1302. After heating an IV fluid in the syringe 1301 as taught in FIGS. 1–12, the syringe is withdrawn and the temperature of its IV fluid contents are indicated by the state of the strip 1302.

OTHER EMBODIMENTS

While there have been shown what are presently considered to be preferred embodiments of the invention, it will be apparent to those skilled in the art that various changes and modifications can be made herein without departing from the scope of the invention as defined by the appended claims.

For example, the invention contemplates application of the present disclosure to thermally cool fluid samples, even though the present disclosure has provided various illustrative examples concerning heating and warming. Furthermore, a variety of thermally-conditioned media may be used pursuant to the invention. Therefore, although naturally-existing air is preferred, other mixtures or substances may be used. The fluid samples heated or cooled by the invention may comprise blood-based materials or non-blood-based materials of considerable variety. Some examples may be sterile saline, anesthetics, nutrients, etc. Further, the invention may warm IV fluid in containers such as vials, bottles, syringes and other elongated tubular structures.

What is claimed is:

1. A thermal-treatment device comprising:
   an inflatable thermal blanket with a passage to carry a stream of thermally-conditioned gas;
   an access port to the passage defined in the inflatable thermal blanket; and
   a self-closing aperture structure acting on the inflatable thermal blanket to sealably receive and support an elongated fluid container in the access port while an end of the container extends through the inflatable structure, wherein the aperture structure comprises a resilient cover layer adhered externally to the inflatable thermal blanket and defining an aperture therethrough, said aperture being aligned with the access port.

2. The device of claim 1, wherein the inflatable thermal blanket includes a plurality of exhaust ports to expel the thermally-conditioned gas.

3. The device of claim 1, further including the elongated fluid container received and supported in the access port by the aperture structure.

4. The device of claim 3, wherein the fluid container comprises a syringe.

5. The device of claim 3, wherein the fluid container comprises a tube.

6. The device of claim 1, wherein the cover layer comprises a layer of synthetic porous foam.

7. The device of claim 1, wherein the cover layer comprises a layer of rubber.

8. The device of claim 1, wherein the cover layer comprises a resilient self-adhesive layer.

9. The device of claim 1, wherein the aperture structure further comprises a layer of adhesive material interposed between the cover and the inflatable structure.

10. The device of claim 1, wherein the access port comprises an aperture defined in the inflatable thermal blanket.

11. The device of claim 1, wherein the access port comprises a perforated pattern defined in the inflatable thermal blanket.

12. The device of claim 1, wherein the access port comprises a region of penetrability defined in the inflatable thermal blanket.

13. The device of claim 1, further comprising a thermometer affixed to the inflatable thermal blanket proximate the aperture structure.

14. The device of claim 13, wherein the thermometer comprises a strip of thermochromic liquid crystals.

15. The device of claim 1, further including the elongated fluid container received and supported in the access port by the aperture structure.

16. The device of claim 15, further including a thermometer on the elongated fluid container.

17. A thermal-treatment device comprising:
an inflatable thermal blanket;
an inflatable structure in the inflatable thermal blanket defining a passage to carry a stream of thermally-conditioned gas and including a plurality of exhaust ports to exhaust the gas into a thermal care zone;
an access port to the passage defined in the inflatable structure;
a resilient self-closing structure acting on the inflatable thermal blanket to sealably receive and support an elongated fluid container in the access port while an end of the container extends through the inflatable structure, wherein the aperture structure comprises a resilient cover layer adhererd externally to the inflatable thermal blanket and defining an aperture therethrough, said aperture being aligned with the access port; and
an inlet in the inflatable thermal blanket to receive the thermally-conditioned gas in the inflatable structure.

18. The thermal care apparatus of claim 17, further including the elongated fluid container received and supported in the access port by the aperture structure.

19. The thermal care apparatus of claim 18, wherein the fluid container comprises a syringe.

20. The thermal care apparatus of claim 18, wherein the fluid container comprises a tube.

21. The thermal care apparatus of claim 17, wherein the cover layer comprises a layer of synthetic porous foam.

22. The thermal care apparatus of claim 17, wherein the cover layer comprises a layer of rubber.

23. The thermal care apparatus of claim 17, wherein the cover layer comprises a resilient self-adhesive layer.

24. The thermal care apparatus of claim 17, wherein the aperture structure further comprises a layer of adhesive material interposed between the cover and the inflatable structure.

25. The thermal care apparatus of claim 17, wherein the access port comprises an aperture defined in the inflatable structure.

26. The thermal care apparatus of claim 17, wherein the access port comprises a perforated pattern defined on the inflatable structure.

27. The thermal care apparatus of claim 17, wherein the access port comprises a region of penetrability defined in the inflatable structure.

28. The thermal care apparatus of claim 17, wherein the inflatable structure comprises one or more inflatable chambers, each defining a plurality of exhaust ports to exhaust the thermally-controlled medium into a thermal care zone.

29. The thermal care apparatus of claim 17, further comprising a thermometer affixed to the inflatable structure proximate the aperture structure.

30. The thermal care apparatus of claim 25, wherein the thermometer comprises a strip of thermochromic liquid crystals.

31. The thermal care apparatus of claim 17, further including the elongated fluid container received and supported in the access port by the aperture structure.

32. The thermal care apparatus of claim 31, further including a thermometer in the elongated fluid container.

33. An inflatable thermal blanket to bathe a patient in a thermally-controlled gas, said blanket including at least one inflatable structure including an inlet to receive the thermally-controlled gas into the structure and also including a plurality of exhaust ports to exhaust the thermally-controlled gas into a thermal care zone, said structure further including a resilient aperture sealably receive and support an elongated fluid container in the access port while an end of the container extends into the structure, wherein the aperture comprises a resilient cover layer adhered externally to the inflatable thermal blanket and defining an aperture therethrough, said aperture being aligned with the access port.

34. The thermal care apparatus of claim 33, further including the elongated fluid container received and supported in the aperture.

35. The thermal care apparatus of claim 34, wherein the fluid container comprises a syringe.

36. The thermal care apparatus of claim 35, wherein the fluid container comprises a tube.

37. The thermal care apparatus of claim 33, wherein the cover layer comprises a layer of synthetic porous foam.

38. The thermal care apparatus of claim 33, wherein the cover layer comprises a layer of rubber.

39. The thermal care apparatus of claim 33, wherein the cover layer comprises a resilient self-adhesive layer.

40. The thermal care apparatus of claim 33, wherein the resilient aperture further comprises a layer of adhesive material interposed between the cover and the structure.

41. The thermal care apparatus of claim 33, wherein the access port comprises an aperture defined in the structure.

42. The thermal care apparatus of claim 33, wherein the access port comprises a perforated pattern defined in the structure.

43. The thermal care apparatus of claim 33, wherein the access port comprises a region of penetrability defined on the structure.

44. The thermal care apparatus of claim 33, wherein the structure comprises one or more inflatable chambers, each defining a plurality of exhaust ports to exhaust the thermally-controlled medium into a thermal care zone.

45. The thermal care apparatus of claim 33, further comprising a thermometer affixed to the structure proximate the aperture structure.

46. The thermal care apparatus of claim 45, wherein the thermometer comprises a strip of thermochromic liquid crystals.

47. The thermal care apparatus of claim 33, further including the elongated fluid container received and supported in the resilient aperture.

48. The thermal care apparatus of claim 47, further including a thermometer on the elongated fluid container.

* * * * *

UNITED STATES PATENT AND TRADEMARK OFFICE
CERTIFICATE OF CORRECTION

PATENT NO. : 5,817,146
DATED : October 6, 1998
INVENTOR(S) : Augustine

It is certified that error appears in the above-identified patent and that said Letters Patent is hereby corrected as shown below:

Column 9, line 44, insert --aperture-- between "self-closing" and "structure".

Signed and Sealed this

Ninth Day of March, 1999

Attest:

Q. TODD DICKINSON

*Attesting Officer*  *Acting Commissioner of Patents and Trademarks*